United States Patent
Chen et al.

(10) Patent No.: US 7,350,416 B2
(45) Date of Patent: Apr. 1, 2008

(54) METHOD FOR DETERMINING PROPERTIES OF A FILM, AND APPARATUS FOR REALIZING THE METHOD

(76) Inventors: Yung-Yu Chen, No. 1, Sec. 4, Roosevelt Rd., Taipei City (TW); Tsung-Tsong Wu, No. 1, Sec. 4, Roosevelt Rd., Taipei City (TW); Guo-Tsai Huang, 3F, No. 388, Pi-Hua St., San-Chung City, Taipei Hsien (TW); Pei-Zen Chang, 1F, No. 26, Lane 60, Sec. 3, Keelung Rd., Ta-An Dist., Taipei City (TW)

( * ) Notice: Subject to any disclaimer, the term of this patent is extended or adjusted under 35 U.S.C. 154(b) by 0 days.

(21) Appl. No.: 11/192,664

(22) Filed: Jul. 29, 2005

(65) Prior Publication Data

US 2006/0172445 A1    Aug. 3, 2006

(30) Foreign Application Priority Data

Jan. 28, 2005    (TW) ............................... 94102857 A (51) Int. Cl.
*G01N 29/00* (2006.01)
*H01L 41/04* (2006.01)
*H01L 41/047* (2006.01)

(52) U.S. Cl. .................... 73/579; 73/24.06; 310/313 B (58) Field of Classification Search ................. 73/579, 73/24.06, 61.75; 310/313 B, 313 D, 313 R; 333/154

See application file for complete search history.

(56) References Cited

U.S. PATENT DOCUMENTS

| | | | | |
|---|---|---|---|---|
| 4,361,026 | A * | 11/1982 | Muller et al. | 73/24.01 |
| 4,635,008 | A * | 1/1987 | Solie | 333/195 |
| 5,162,689 | A * | 11/1992 | Fliegel et al. | 310/313 B |
| 5,568,001 | A * | 10/1996 | Davenport | 310/313 R |
| 5,793,146 | A * | 8/1998 | Wright | 310/313 B |
| 6,688,158 | B2 * | 2/2004 | Cunningham et al. | 73/24.06 |
| 6,946,932 | B2 * | 9/2005 | Takagi et al. | 333/195 |
| 7,135,805 | B2 * | 11/2006 | Yamanouchi | 310/313 D |
| 7,148,610 | B2 * | 12/2006 | Jacot et al. | 310/364 |
| 7,239,067 | B2 * | 7/2007 | Komuro et al. | 310/340 |
| 2004/0222717 | A1 * | 11/2004 | Matsuda et al. | 310/313 R |

OTHER PUBLICATIONS

Wu, T. T., et al., "Evaluation of elastic properties of submicrometer thin films using slanted finger interdigital transducers," Journal of Applied Physics 97, 073510 (2005).

* cited by examiner

*Primary Examiner*—Hezron Williams
*Assistant Examiner*—Jacques M. Saint-Surin
(74) *Attorney, Agent, or Firm*—Ladas & Parry LLP (57) ABSTRACT

A method for determining properties or a thin film includes the steps of: providing a piezoelectric substrate; providing a slanted finger interdigital transducer unit that includes a transmitter port and a receiver port on the piezoelectric substrate; forming the thin film on the piezoelectric substrate between the transmitter port and the receiver port; applying an input signal to the transmitter port; and measuring a phase difference, which corresponds to the input signal, from the receiver port. Accordingly, properties of the thin film are determined based on the measured phase difference. An apparatus for realizing the method is also disclosed.

5 Claims, 11 Drawing Sheets

METHOD FOR DETERMINING PROPERTIES OF A FILM, AND APPARATUS FOR REALIZING THE METHOD

CROSS-REFERENCE TO RELATED APPLICATION

This application claims priority of Taiwanese application No. 094102857, filed on Jan. 28, 2005.

FIELD OF THE INVENTION

This invention relates to a method for determining properties of a thin film, more particularly to a method for determining properties of a thin film using surface acoustic wave.

DESCRIPTION OF THE RELATED ART

Accurate determination of film properties is very important in semiconductor and micro electro-mechanical system industries.

In a conventional method for determining the properties of a thin film, a quartz resonator is used to monitor the deposition of the thin film on a substrate, and to control the amount of the thin film deposited on the substrate and the rate at which the thin film is deposited on the substrate. However, the quartz resonator is required to have a relatively large size to operate accurately.

To solve this problem, in U.S. Pat. No. 6,651,488, it has been proposed to use a thin film acoustic resonator, in place of the quartz resonator. However, the thin film acoustic resonator, unlike the quartz resonator, is unable to control the rate at which the thin film is deposited on the substrate.

In IEEE UFFC periodical, Motorola addresses the problem by proposing the use of interdigital transducers (IDT) that is operable so as to generate a surface acoustic wave. However, in order to be able to measure the frequency response induced by the surface acoustic wave, the thin film is required to be deposited on both the substrate and the IDT. As such, the conventional method is suitable only for dielectric thin films.

SUMMARY OF THE INVENTION

Therefore, the object of the present invention is to provide a method for determining properties of a film that can overcome the aforesaid drawbacks of the prior art.

Another object of the present invention is to provide an apparatus that can be used to determine properties of a thin film.

According to one aspect of the present invention, a method for determining properties of a thin film comprises the steps of:

A) providing a piezoelectric substrate;

B) providing a slanted finger interdigital transducer unit that includes a transmitter port and a receiver port on the piezoelectric substrate;

C) forming the thin film on the piezoelectric substrate between the transmitter port and the receiver port;

D) applying an input signal to the transmitter port; and

E) measuring a phase difference, which corresponds to the input signal applied in step D), from the receiver port;

wherein properties of the thin film are determined based on the phase difference measured in step E).

According to another aspect of the present invention, an apparatus for determining properties of a thin film comprises a piezoelectric substrate, a slanted finger interdigital transducer unit, and a mask. The slanted finger interdigital transducer unit includes a transmitter port and a receiver port, each of which is provided on a surface of the piezoelectric substrate. The mask is disposed above the surface of the piezoelectric substrate, and defines a hole therethrough to expose a portion of the surface of the piezoelectric substrate between the transmitter port and the receiver port.

BRIEF DESCRIPTION OF THE DRAWINGS

Other features and advantages of the present invention will become apparent in the following detailed description of the preferred embodiments with reference to the accompanying drawings, of which.

DETAILED DESCRIPTION OF THE PREFERRED EMBODIMENTS

Before the present invention is described in greater detail, it could be noted that like elements are denoted by the same reference numerals throughout the disclosure.

Figure 1:
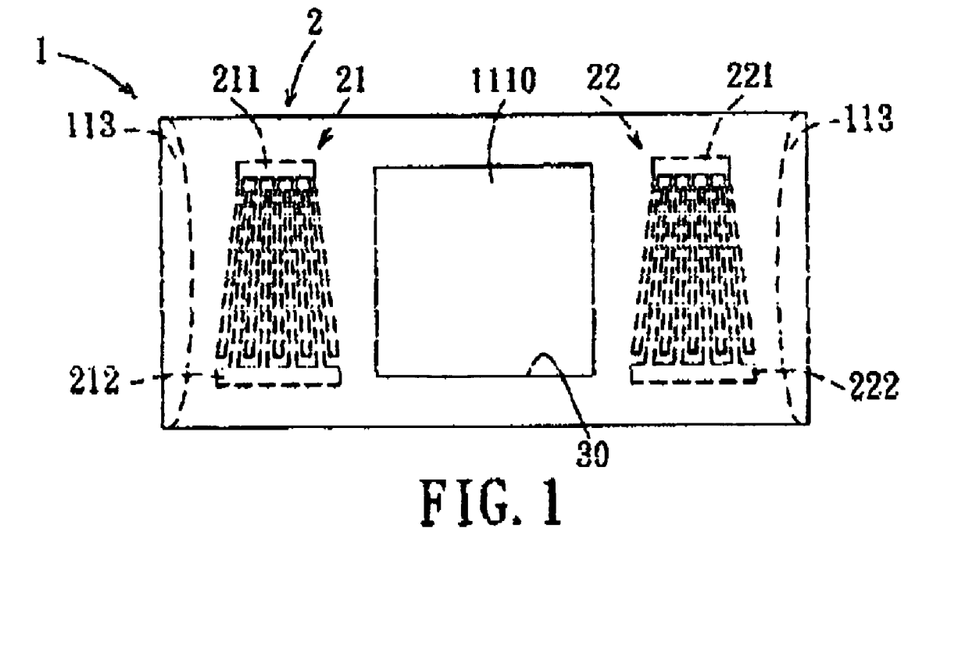
FIG. 1 is a schematic view of the first preferred embodiment of an apparatus for determining properties of a thin film according to the present invention.
Figure 2:
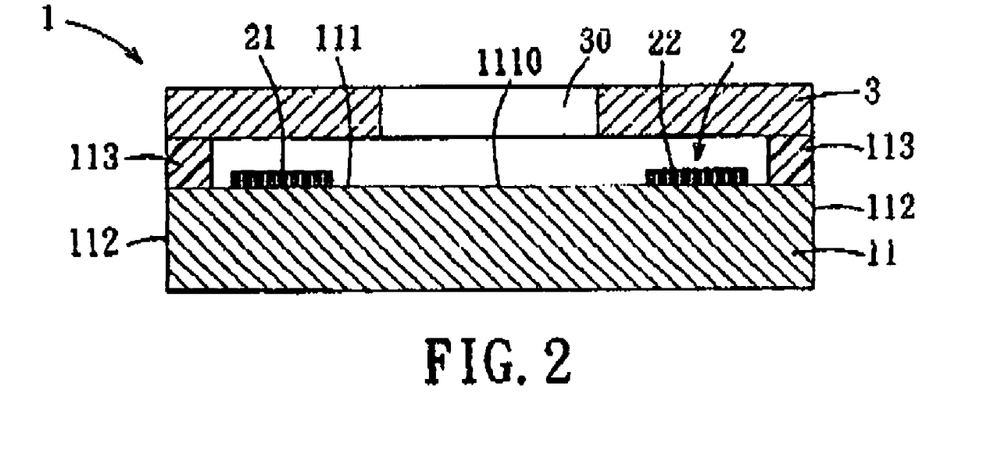
FIG. 2 is a schematic sectional view of the first preferred embodiment.

Referring to FIGS. 1 and 2, the first preferred embodiment of an apparatus 1 according to this invention is shown to include a piezoelectric substrate 11, a pair of acoustic absorbers 113, a slanted finger interdigital transducer unit 2, and a mask 3.

The apparatus 1 is used for determining properties, e.g., thickness, density, and elastic contants, of a thin film 5 (see FIG. 4), in a manner to be described hereinafter.

The piezoelectric substrate 11 has a surface 111 that has opposite edges 112. In this embodiment, the piezoelectric substrate 11 is made from $LiNbO_3$. In an alternative embodiment, the piezoelectric substrate 11 may be made from one, or a mixture of two or more of the following compositions: AlN, GaAs, ZnO, LiTaO$_3$, and lead zirconate titanate (PZT).

Each of the acoustic absorbers 113 is provided on the surface 111 of the piezoelectric substrate 11 at a respective one of the opposite edges 112 of the piezoelectric substrate 11. In this embodiment, each of the acoustic absorbers 113 is made from rubber The slanted finger interdigital transducer unit 2 is provided on the surface 111 of the piezoelectric substrate 11. In this embodiment, the slanted finger interdigital transducer unit 2 includes a first transmitter port 21 and a first receiver port 22, each of which is disposed proximate to the respective one of the opposite edges 112 of the piezoelectric substrate 11. As beat shown in FIG. 1, each of the first is transmitter port 21 and the first receiver port 22 includes a pair of electrodes 211, 212, 221, 222, each of which has a plurality of electrode fingers. The electrode fingers of the electrodes 211, 212 of the first transmitter port 21 are arranged so as to interleave with each other. Similarly, the electrode fingers of the electrodes 221, 222 of the first receiver port 22 are arranged so as to interleave with each other. Preferably, each of the first transmitter port 21 and the first receiver port 22 of the slanted finger interdigital transducer unit 2 is made from aluminum.

The mask 3 is disposed above the surface 111 of the piezoelectric substrate 21 on the acoustic absorbers 113, and is formed with a hole 30 therethrough to expose a portion 1110 of the surface 111 of the piezoelectric substrate 11, which is between the first transmitter port 21 and the first receiver port 22.

Figure 3A:
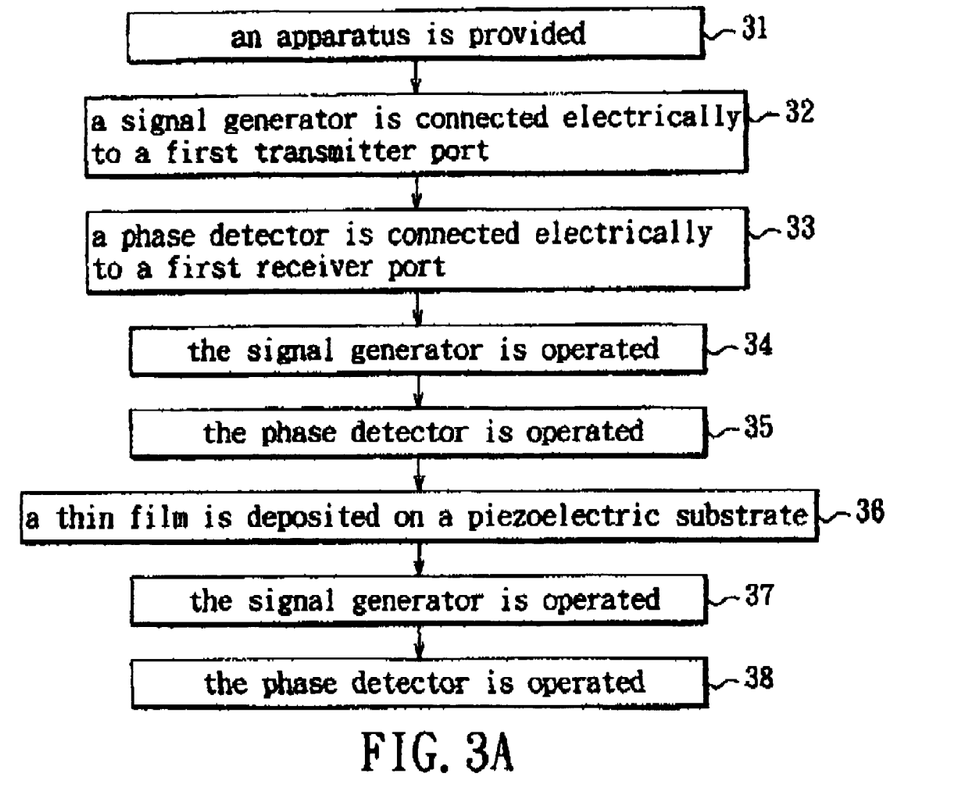
FIGS. 3A and 3B are flowchart to illustrate the first preferred embodiment of a method for determining properties of a thin film according to the present invention.
Figure 3B:
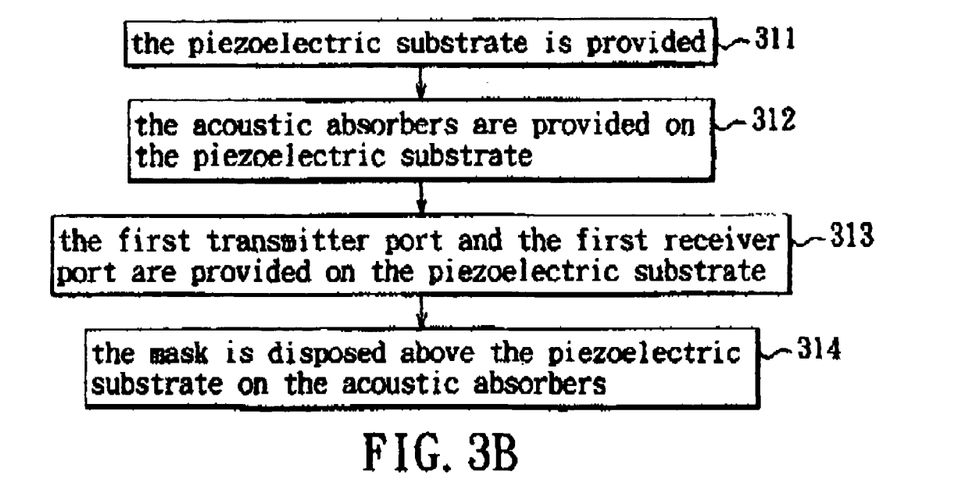

The first preferred embodiment of a method for determining properties of the thin film 5 according to this invention will now be described with further reference to FIGS. 3A and 3B.

In step 31, the apparatus 1 is provided.

In this embodiment, step 31 includes the following sub-step:

sub-step 311: providing the piezoelectric substrate 11;

sub-step 312: providing the acoustic absorbers 113 on the surface 111 of the piezoelectric substrate 11;

sub-step 313: providing the first transmitter port 21 and the first receiver port 22 on the surface 111 of the piezoelectric substrate 11; and sub-step 314: disposing the mask 3 above the surface 111 of the piezoelectric substrate 11 on the acoustic absorbers 113.

Figure 4:
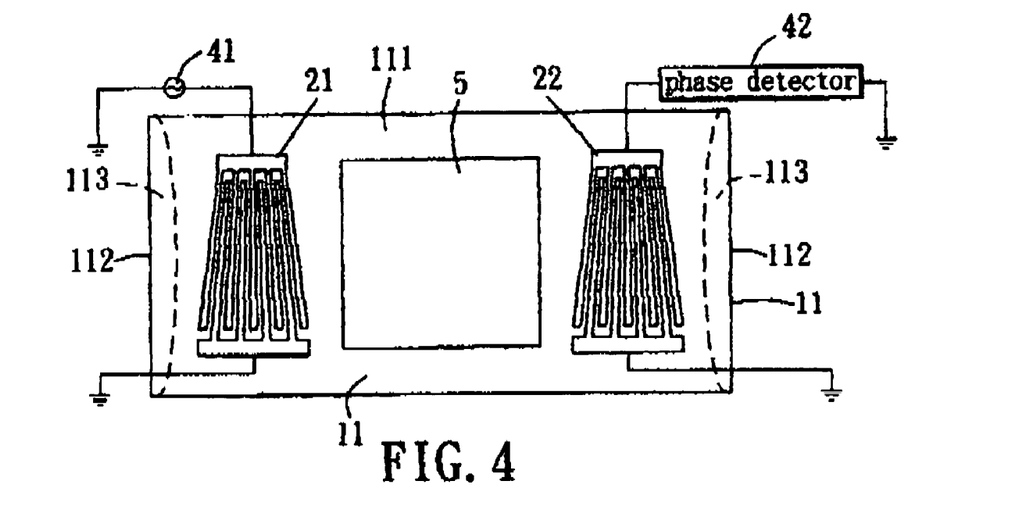
FIG. 4 is a schematic view of the apparatus of the first preferred embodiment in a state of use.

In step 32, as illustrated in FIG. 4, a signal generator 42 is connected electrically to the first transmitter port 21.

In step 33, a phase detector 42 is connected electrically to the first receiver port 22.

In step 34, the signal generator 41 is operated so as to apply an input signal to the first transmitter port 21 to result in a surface acoustic wave being generated from the first transmitter port 21. The surface acoustic wave travels on the surface 111 of the piezoelectric substrate 11 and is subsequently received by the first receiver port 21.

It is noted that the acoustic absorbers 113 minimize the wave reflections caused by the edges 112 of the surface 111 of the piezoelectric substrate 11.

In step 35, the phase detector 42 is operated so as to measure a phase difference, which corresponds to the input signal applied in step 34, and which is induced by the surface acoustic wave traveling on the surface 111 of the piezoelectric substrate 11.

In step 36, the thin film 5 is deposited on the exposed portion 1110 of the surface 111 of the piezoelectric substrate 11.

In this embodiment, step 36 is performed using sputtering technique. In an alternative embodiment, step 36 is performed using one of thermal evaporation technique, chemical vapor deposition (CVD) technique, and molecular beam epitaxy (MBS) technique.

In step 37, the signal generator 41 is operated once again so as to apply an input signal to the first transmitter port 21 to result in a surface acoustic wave being generated from the first transmitter port 21. The surface acoustic wave travels on the surface 111 of the piezoelectric substrate 11 and the thin film 5, and is subsequently received by the first receiver port 22.

In step 38, the phase detector 42 is operated once again so as to measure a phase difference, which corresponds to the input signal applied in step 37, and which is induced by the surface acoustic wave traveling on the surface 111 of the piezoelectric substrate 11 and the thin film 5.

Accordingly, the properties of the thin film 5 may be determined based on the phase difference measured in step 35 and the phase difference measured in step 38.

Since the thin film 5 is deposited free of contacts from the slanted finger interdigital transducer unit 2, the aforementioned method of this invention may be applied to both dielectric and metallic thin films.

Figure 5:
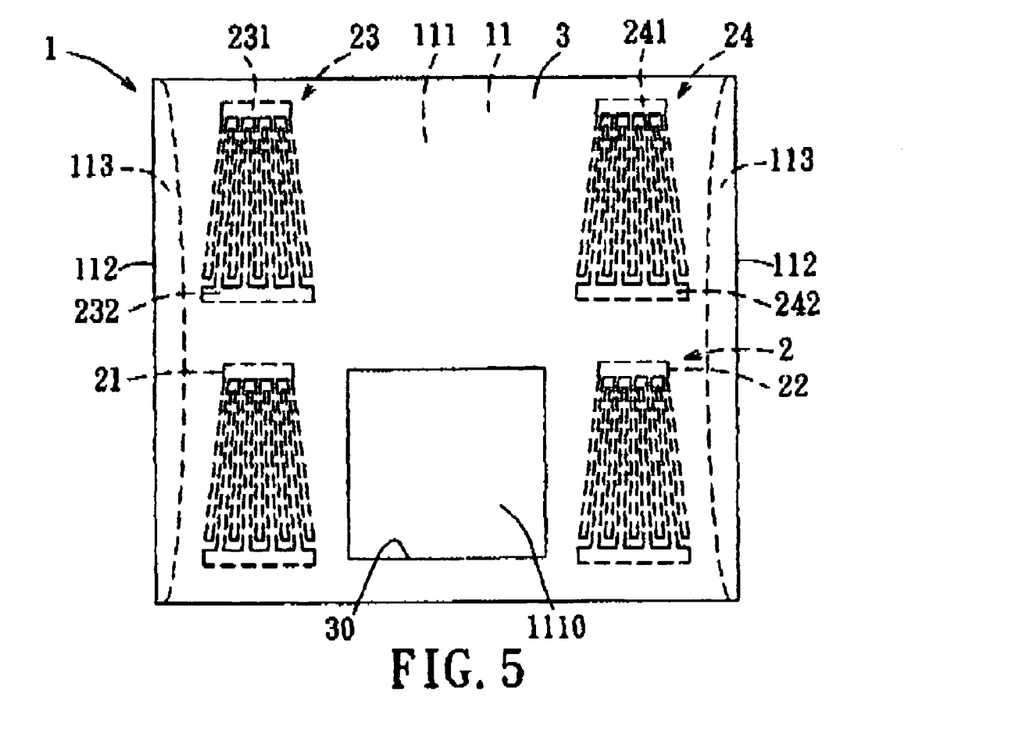
FIG. 5 is a schematic view of the second preferred embodiment of an apparatus for determining properties of a thin film according to the present invention.

FIG. 5 illustrates the second preferred embodiment of an apparatus 1 according to this invention. When compared to the previous embodiment, the slanted finger interdigital transducer unit 2 further includes a second transmitter port 23 and a second receiver port 24, each of which is disposed proximate to a respective one of the opposite edges 112 of the piezoelectric substrate 11. It is noted that a first distance between the first transmitter port 21 and the first transmitter port 22 is equal to a second distance between the second transmitter port 23 and the second receiver port 24.

Like the first transmitter port 21 and the first receiver port 22, each of the second transmitter port 23 and the second receiver port 24 includes a pair of electrodes 231, 232, 241, 242, each of which has a plurality of electrode fingers. The electrode fingers of the electrodes 231, 232 of the second transmitter port 23 are arranged so an to interleave with each other. Similarly, the electrode fingers of the electrodes 241, 242 of the second receiver port 24 are arranged so as to interleave with each other. Preferably, each of the second transmitter port 23 and the second receiver port 24 is made from aluminum.

Figure 6A:
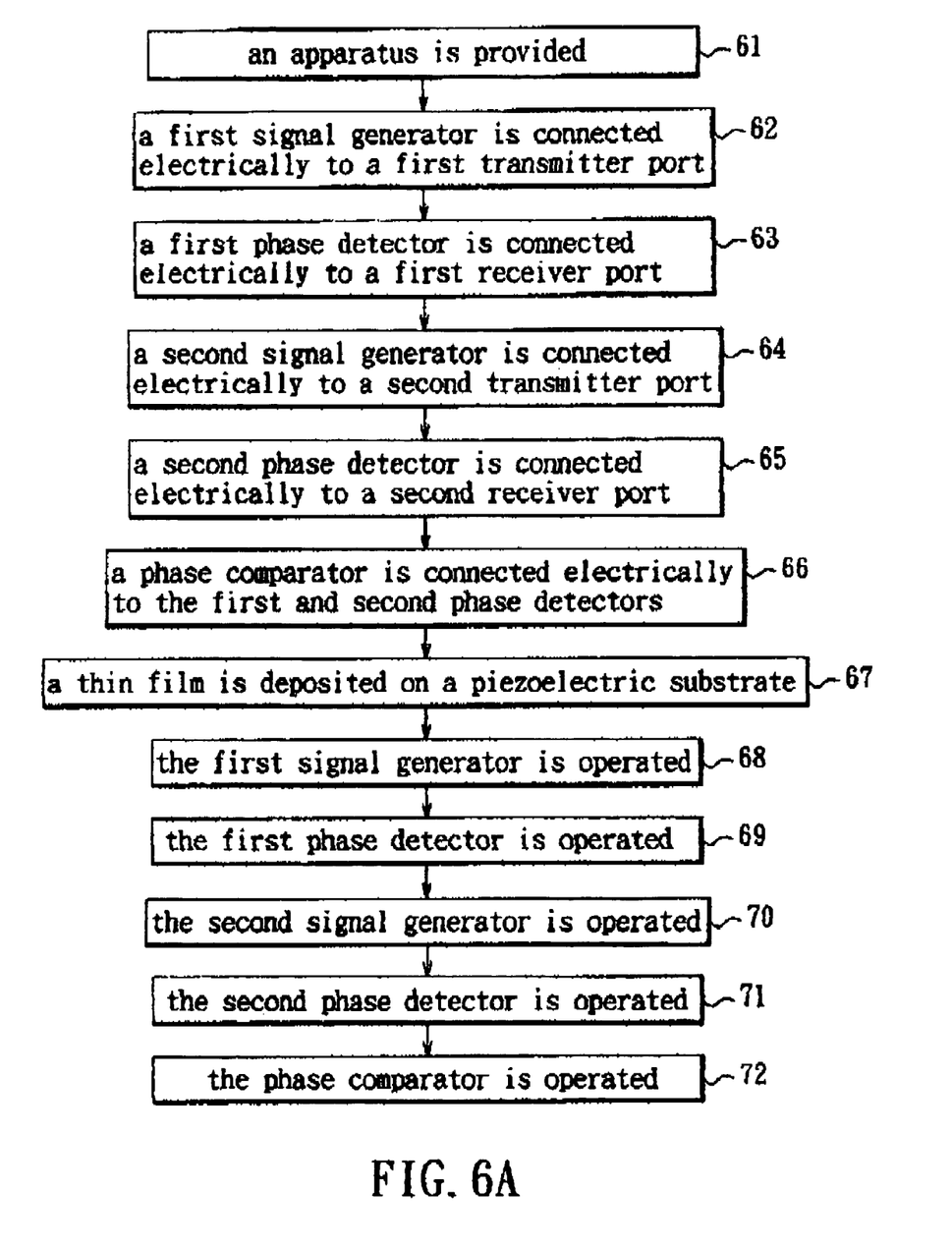
FIGS. 6A and 6B are flowcharts to illustrate the second preferred embodiment of a method for determining properties of a thin film according to the present invention.
Figure 6B:
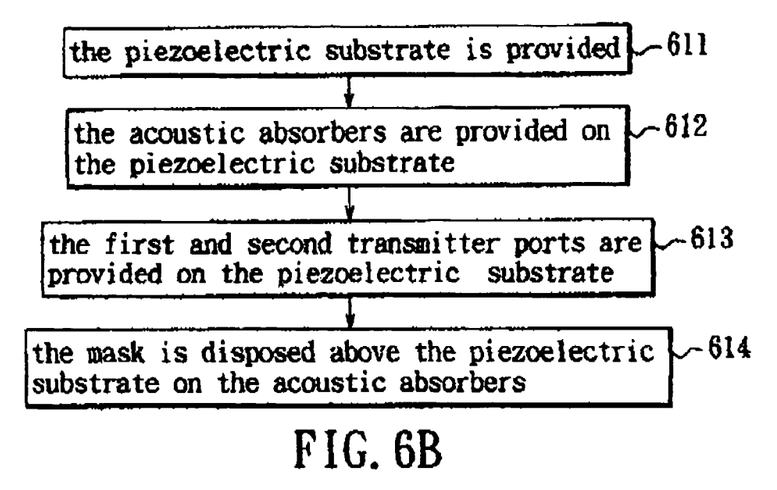

The second preferred embodiment of a method for determining properties of the thin film 5 according to is this invention will now be described with further reference to FIGS. 6A and 6B.

In step 61, the apparatus 1 is provided.

In this embodiment, step 61 includes the following sub-steps:

sub-step 611: providing the piezoelectric substrate 11;

sub-step 612: providing the acoustic absorbers 113 on the surface 111 of the piezoelectric substrate 11;

sub-step 613: providing the first and second transmitter ports 21, 23, and the first and second receiver ports 22, 24 on the surface 111 of the piezoelectric substrate 11; and sub-step 614: disposing the mark 3 above the surface 111 of the piezoelectric substrate 11 on the acoustic absorbers 113.

Figure 7:
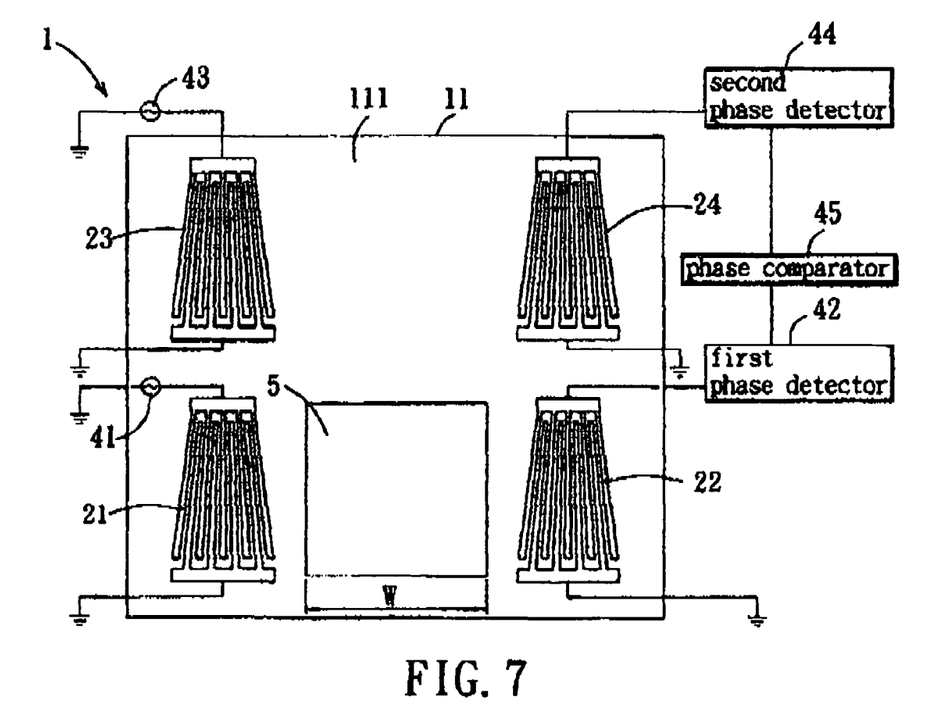
FIG. 7 is a schematic view of the apparatus of the second preferred embodiment in a state of use.

In step 62, as illustrated in FIG. 7, a first signal generator 41 is connected electrically to the first transmitter port 21.

In step 63, a first phase detector 42 is connected electrically to the first receiver port 22.

In step 64, a second signal generator 43 is connected electrically to the second transmitter port 23.

In step 65, a second phase detector 44 is connected electrically to the second receiver port 24.

In step 66, a phase comparator 45 is connected electrically to the first and second phase detectors is 42, 44.

In step 67, the thin film 5 is deposited on the exposed portion 1110 of the surface 111 of the piezoelectric substrate 11.

In step 68, the first signal generator 41 is operated so as to apply an input signal to the first transmitter port 21 to result in a surface acoustic wave being generated from the first transmitter port 21. The surface acoustic wave travels on the surface 111 of the piezoelectric substrate 11 and the thin film 5, and is subsequently received by the first receiver port 22.

In step 69, the first phase detector 42 is operated so as to measure a first phase difference, which corresponds to the input signal applied in step 68, and which is induced by the surface acoustic wave traveling on the surface 111 of the piezoelectric substrate 11 and the thin film 5.

In step 70, the second signal generator 43 is operated so as to apply an input signal to the second transmitter port 23 to result in a surface acoustic wave being generated from the second transmitter port 23. The surface acoustic wave travels on the surface 111 of the piezoelectric substrate 11, and is subsequently received by the second receiver port 24.

In step 71, the second phase detector 44 is operated so as to measure a second phase difference, which corresponds to the input signal applied in step 70, and which is induced by the surface acoustic wave traveling on the surface 111 of the piezoelectric substrate 11.

In step 72, the phase comparator 45 is operated so as to measure a phase difference between the first phase difference measured in step 69 and the second phase difference measured in step 71.

Accordingly, the properties of the thin film 5 may be determined based on the phase difference obtained in step 72, in a manner to be described hereinafter.

Since the phase velocity of the surface acoustic wave on the surface 111 of the piezoelectric substrate 11 is constant once the phase difference is obtained, the phase velocity of the surface acoustic wave on the surface 111 of the piezoelectric substrate 11 and the thin film 5 may be calculated from the formula, $$V_2 = 1/(\Delta\phi/2\pi f w + 1/V_3) \quad (1)$$

where $V_2$ is the phase velocity of the surface acoustic wave on the surface 111 of the piezoelectric substrate 11 and the thin film 5, $\Delta\phi$ is the phase difference obtained in step 72, f is the resonance frequency of the surface acoustic wave, w is the width of the thin film 5, and $V_1$ is the phase velocity of the surface acoustic wave on the surface 111 of the piezoelectric substrate 11.

Figure 8:
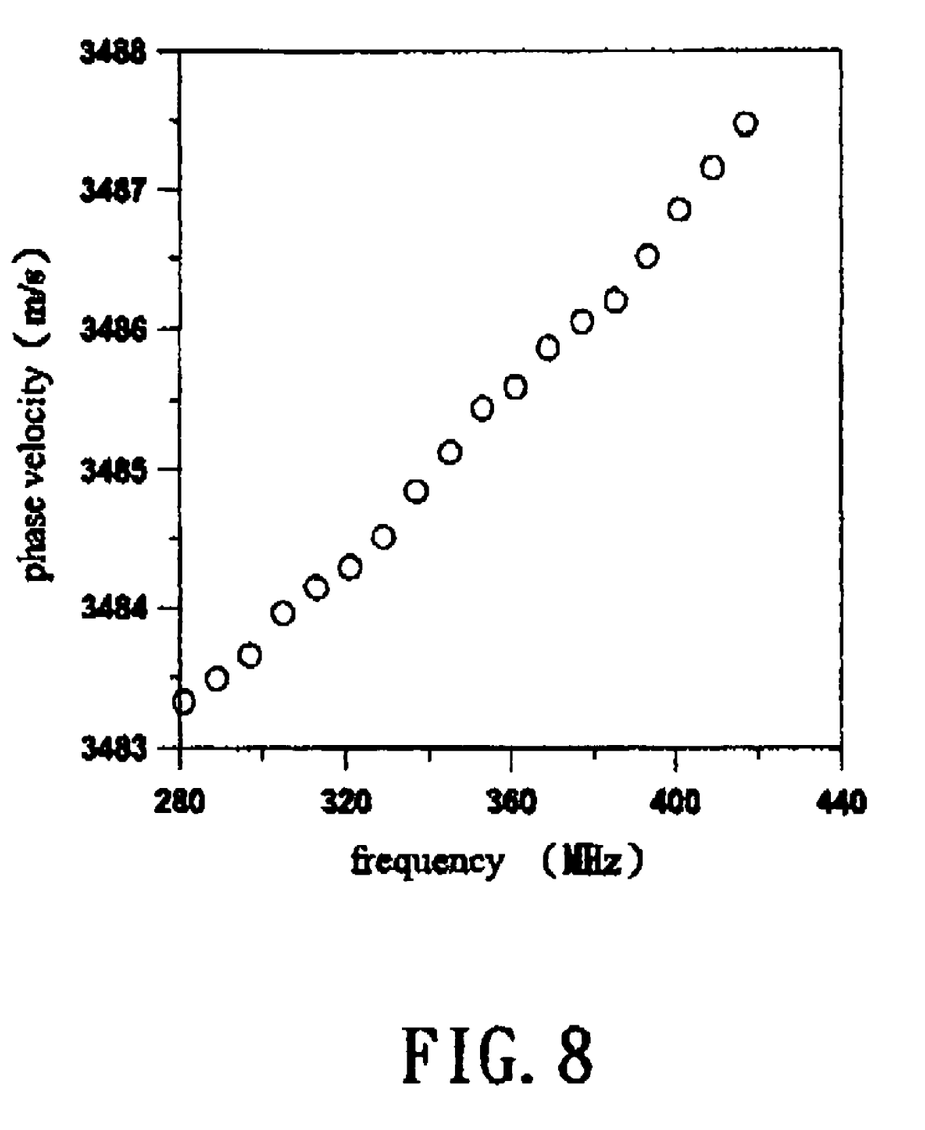
FIG. 8 is a plot to illustrate a dispersion curve of a surface acoustic wave.

Using Formula (1), a dispersion curve, as illustrated in FIG. 8, of the surface acoustic wave on the surface 111 of the piezoelectric substrate 11 and the thin film 5 may be obtained.

Figure 9:
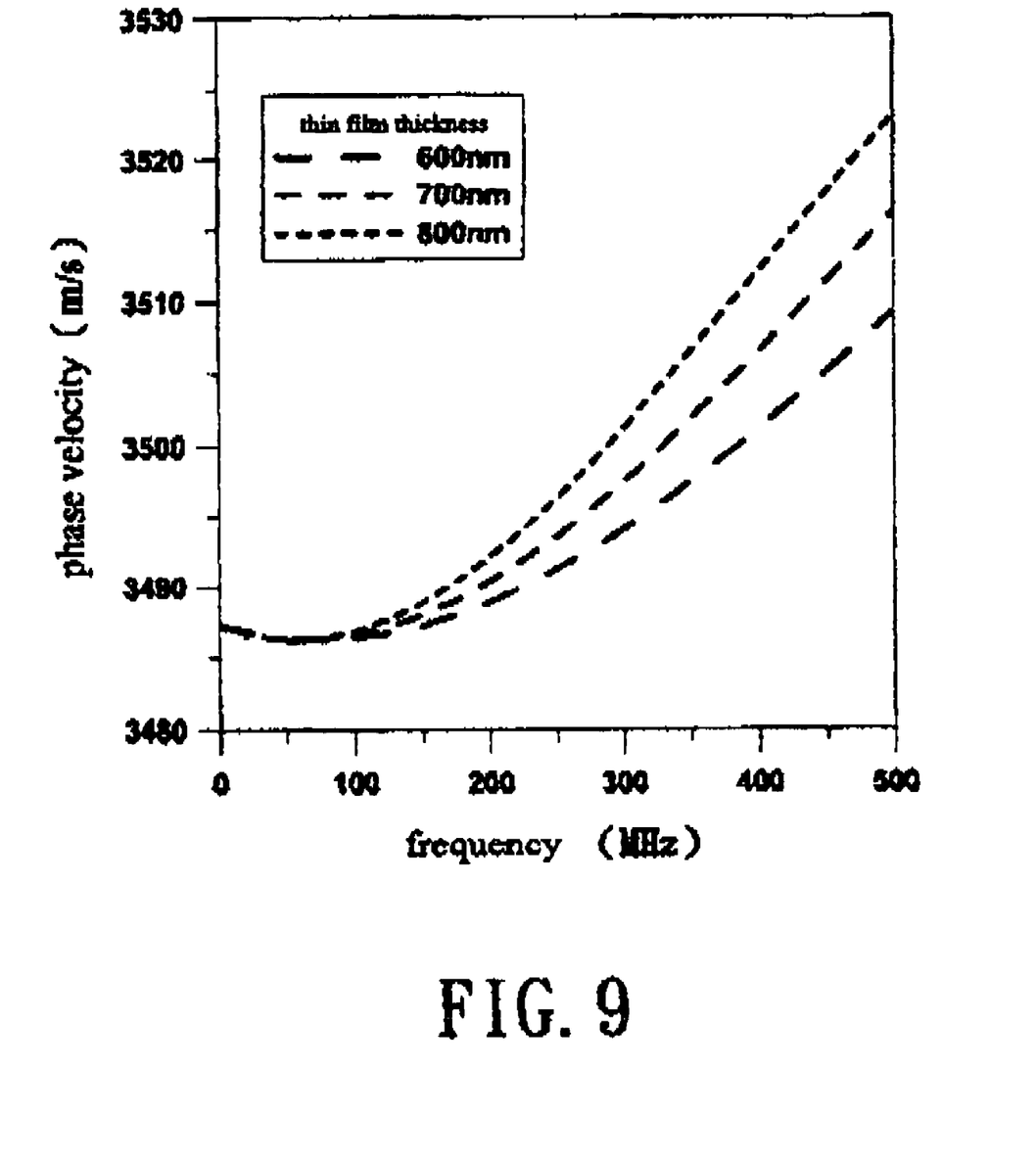
FIG. 9 is a plot to illustrate dispersion curves for thin films with different thicknesses.

FIG. 9 illustrates different dispersion curves obtained for different thicknesses of the thin film 5. As such, the thickness of the thin film 5 may be determined based on the dispersion curve. Furthermore, based on the dispersion curve, the density and elastic constants of the thin film 5 may be determined by using the Simplex method.

Figure 10:
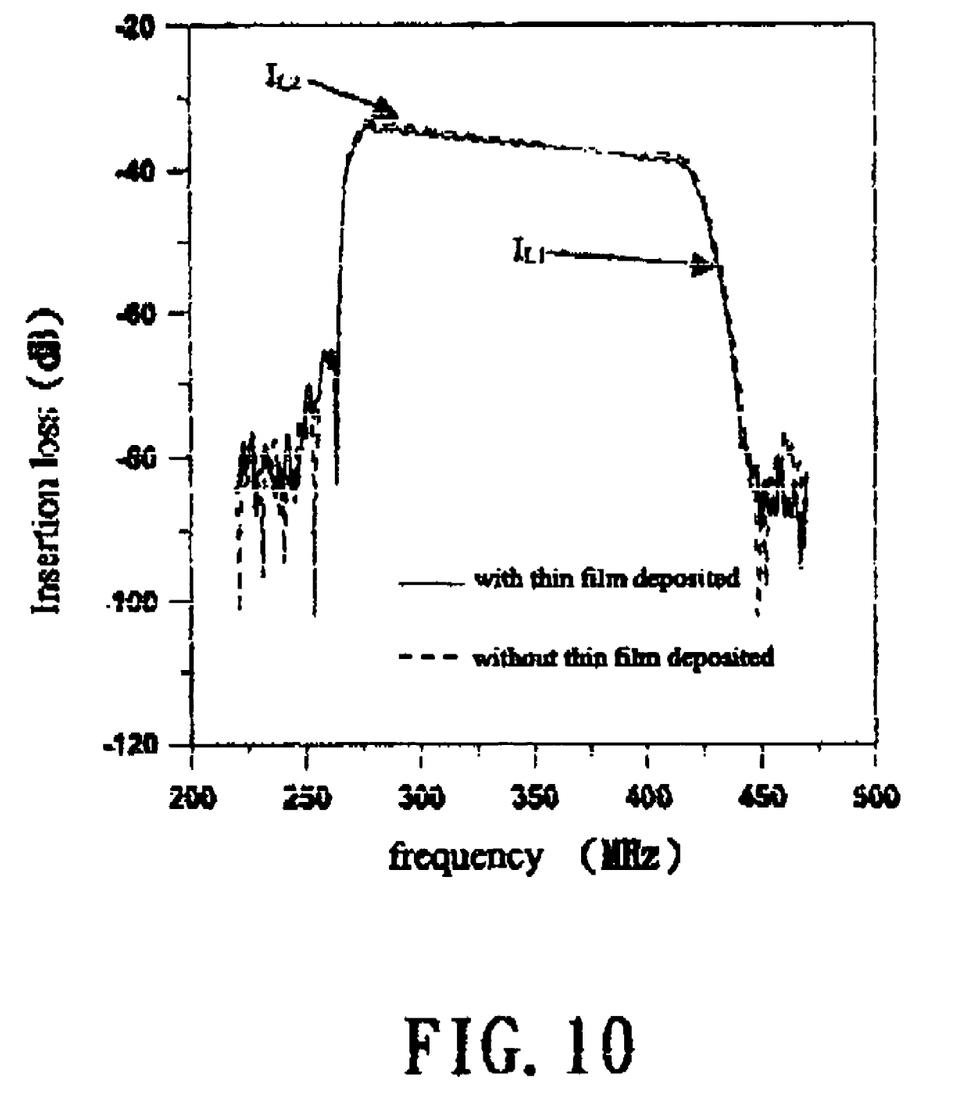
FIG. 10 is a plot to illustrate insertion losses of a slanted finger interdigital transducer module of the second preffered embodiment.

FIG. 10 illustrates the insertion losses ($I_{L1}$, $I_{L2}$) of the slanted linger interdigital transducer unit 2 before and after the deposition of the thin film 5. It can be deduced that the deposition of the thin film 5 does not affect the insertion loss of the slanted finger interdigital transducer unit 2. It is noted that the insertion loss of the slanted finger interdigital transducer unit 2 was measured using a network analyzer, such as the Agilent 8714ES network analyzer.

Figure 11:
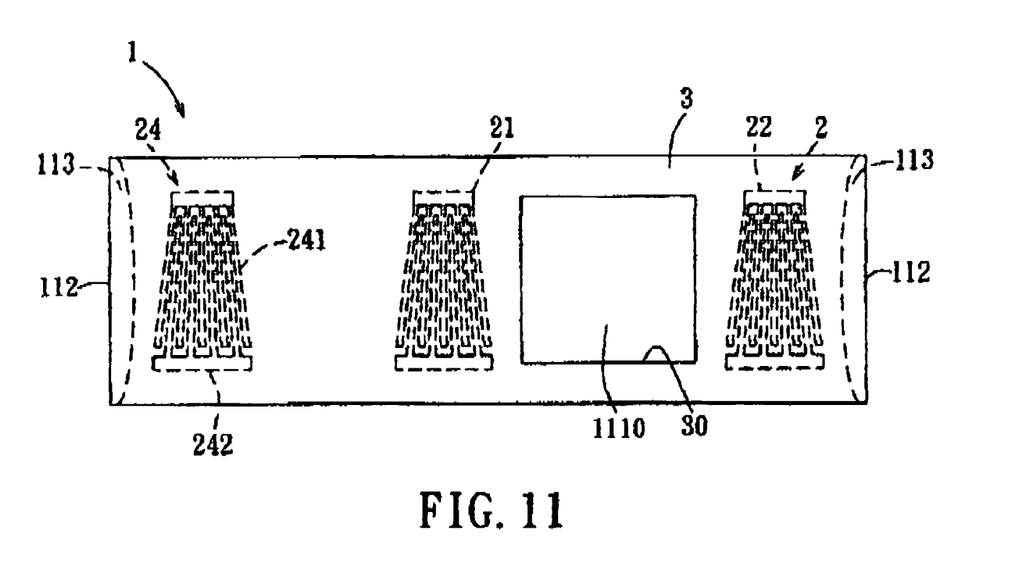
FIG. 11 is a schematic view of the third preferred embodiment of an apparatus for determining properties of a thin film according to the present invention.

FIG. 11 illustrates the third preferred embodiment of an apparatus 1 according to this invention. When compared to the first embodiment, the slanted finger interdigital transducer unit further includes a second receiver port 24. Each of the first and second receiver ports 22, 24 is disposed proximate to the respective one of the edges 112 of the surface 111 of the piezoelectric substrate 11. The first transmitter port 21 is disposed between the first and second receiver ports 22, 24.

Like the first receiver port 22, the second receiver port 24 includes a pair of electrodes 241, 242, each of which has a plurality of electrode fingers. The electrode fingers of the electrodes 241, 242 or the second receiver port 24 are arranged so as to interleave with each other.

Figure 12A:
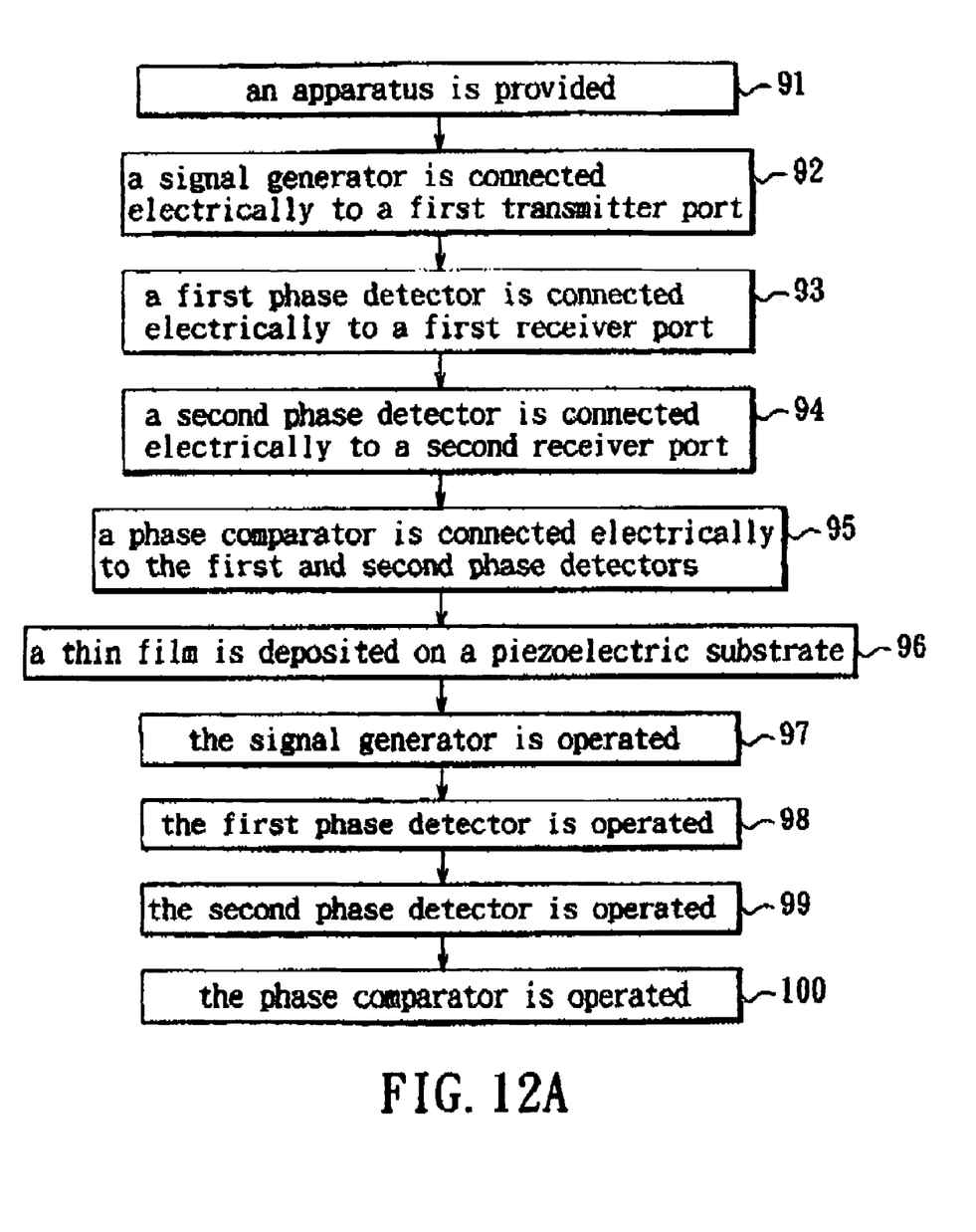
FIGS. 12A and 12B are flowcharts to illustrate the third preferred embodiment of a method for determining properties of a thin film according to the present invention.
Figure 12B:
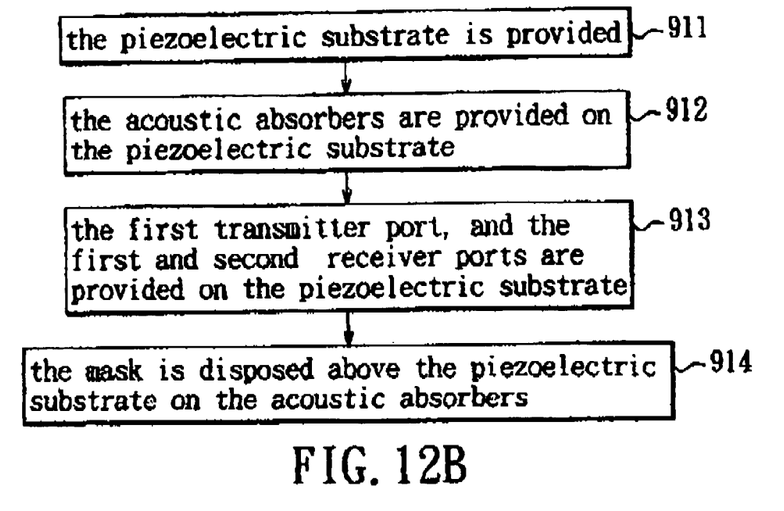

The third preferred embodiment of a method for determining properties of the thin film 5 according to this invention will now be described with further reference to FIGS. 12A and 12B.

In step 91, the apparatus 1 is provided.

In this embodiment, step 91 includes the following sub-steps:

sub-step 911: providing the piezoelectric substrate 11;

sub-step 912: providing the acoustic absorbers 113 on the surface 111 of the piezoelectric substrate 11;

sub-step 913: providing the first transmitter port 21, and the first and second receiver ports 22, 24 on the surface 111 of the piezoelectric substrate 11; and sub-step 914: disposing the mask 3 above the surface 111 of the piezoelectric substrate 11 on the acoustic absorbers 113.

Figure 13:
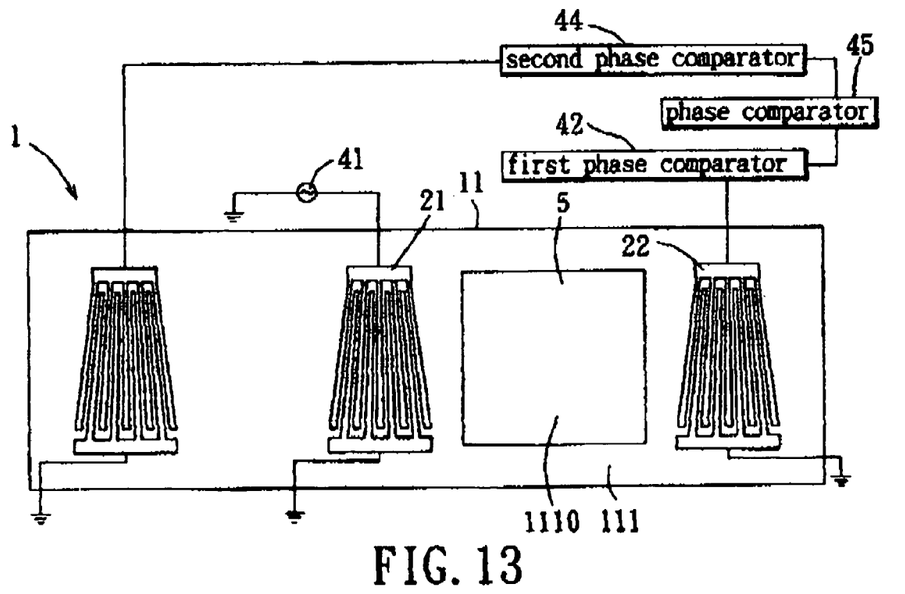
FIG. 13 in a schematic view of the apparatus of the third preferred embodiment in a state of use.

In step 92, as illustrated in FIG. 13, a signal generator 41 is connected electrically to the first transmitter port 21.

In step 93, a first phase detector 42 is connected electrically to the first receiver port 22.

In step 94, a second phase detector 44 is connected electrically to the second receiver port 24.

In step 95, a phase comparator 45 is connected electrically to the first and second phase detectors 42, 44.

In step 96, the thin films is deposited on the exposed portion 1110 of the surface 111 of the piezoelectric substrate 11.

In step 97, the signal generator 41 is operated no as to apply an input signal to the first transmitter port 21 to result in a surface acoustic wave being generated from the first transmitter port 21. The surface acoustic wave is subsequently received by the first and second receiver ports 22, 24.

In step 98, the first phase detector 42 in operated so as to measure a first phase difference, which corresponds to the input signal applied in step 97, and which is induced by the surface acoustic wave traveling on the surface 111 of the piezoelectric substrate 11 and the thin film 5.

In step 99, the second phase detector 44 in operated so as to measure a second phase difference, which corresponds to the input signal applied in stop 97, and which is induced by the surface acoustic wave traveling on the surface 111 of the piezoelectric substrate 11.

In step 100, the phase comparator 45 is operated so as to measure a phase difference between the first phase difference measured in step 98 and the second phase difference measured in step 99.

Accordingly, the properties of the thin film 5 may be determined based on the phase difference obtained in step 100.

While the present invention has been described in connection with what is considered the most practical and preferred embodiments. it is understood that this invention is not limited to the disclosed embodiments but is intended to cover various arrangements included within the spirit and scope of the broadest interpretation so as to encompass all such modifications and equivalent arrangements.

What is claimed is:

1. An apparatus for determining properties of a thin film, said apparatus comprising:
   a piezoelectric substrate having a surface;
   a slanted finger interdigital transducer unit provided on said surface of said piezoelectric substrate, and including
      a first transmitter port that includes first and second electrodes, each of which includes a plurality of electrode fingers, each of said electrode fingers of each of said first and second electrodes of said first transmitter port having opposite first and second ends,
      said first ends of adjacent ones of said electrode fingers of said first electrode of said first transmitter port defining a distance therebetween that is less than that between said second ends of said adjacent ones of said electrode fingers of said first electrode of said first transmitter port,
      said first ends of adjacent ones of said electrode fingers of said second electrode of said first transmitter port defining a distance therebetween that is greater than that between said second ends of said adjacent ones of said electrode fingers of said second electrode of said first transmitter port, and
      a first receiver port that includes first and second electrodes, each of which includes a plurality of electrode fingers, each of said electrode fingers of each of said first and second electrodes of said first receiver port having opposite first and second ends,
      said first ends of adjacent ones of said electrode fingers of said first electrode of said first receiver port defining a distance therebetween that is less than that between said second ends of said adjacent ones of said electrode fingers of said first electrode of said first receiver port,
      said first ends of adjacent ones of said electrode fingers of said second electrode of said first receiver port defining a distance therebetween that is greater than that
      between said second ends of said adjacent ones of said electrode fingers of said second electrode of said first receiver port; and
   a mask disposed above said surface of said piezoelectric substrate, and defining a hole therethrough to expose a portion of said surface of said piezoelectric substrate between said first transmitter port and said first receiver port.

2. The apparatus as claimed in claim 1, wherein said piezoelectric substrate further has opposite edges, said apparatus further comprising a pair of acoustic absorbers, each of which is provided on said surface of said piezoelectric surface and is disposed at a respective one of said edges of said piezoelectric substrate.

3. The apparatus as claimed in claim 1, wherein said slanted finger interdigital transducer unit further includes
   a second transmitter port that includes first and second electrodes, each of which includes a plurality of electrode fingers, each of said electrode fingers of each of said first and second electrodes of said second transmitter port having opposite first and second ends, said first ends of adjacent ones of said electrode fingers of said first electrode of said second transmitter port defining a distance therebetween that is less than that between said second ends of said adjacent ones of said electrode fingers of said first electrode of said second transmitter port,
   said first ends of adjacent ones of said electrode fingers of said second electrode of said second transmitter port defining a distance therebetween that is greater than that between said second ends of said adjacent ones of said electrode fingers of said second electrode of said second transmitter port, and
   a second receiver port that includes first and second electrodes, each of which includes a plurality of electrode fingers, each of said electrode fingers of each of said first and second electrodes of said second receiver port having opposite first and second ends,
   said first ends of adjacent ones of said electrode fingers of said first electrode of said second receiver port defining a distance therebetween that is less than that between said second ends of said adjacent ones of said electrode fingers of said first electrode of said second receiver port,
   said first ends of adjacent ones of said electrode fingers of said second electrode of said second receiver port defining a distance therebetween that is greater than that between said second ends of said adjacent ones of said electrode fingers of said second electrode of said second receiver port.

4. The apparatus as claimed in claim 3, wherein said first transmitter port and said first receiver port define a first distance therebetween, said second transmitter port and said second receiver port defining a second distance therebetween that is equal to the first distance between said first transmitter port and said first receiver port.

5. The apparatus as claimed in claim 1, wherein said slanted finger interdigital transducer unit further includes a second receiver port that includes first and second electrodes, each of which includes a plurality of electrode fingers, each of said electrode fingers of each of said first and second electrodes of said second receiver port having opposite first and second ends,
   said first ends of adjacent ones of said electrode fingers of said first electrode of said second receiver port defining a distance therebetween that is less than that between said second ends of said adjacent ones of said electrode fingers of said first electrode of said second receiver port,
   said first ends of adjacent ones of said electrode fingers of said second electrode of said second receiver port defining a distance therebetween that is greater than that between said second ends of said adjacent ones of said electrode fingers of said second electrode of said second receiver port.

* * * * *